United States Patent
O'Hare et al.

(10) Patent No.: US 6,184,038 B1
(45) Date of Patent: *Feb. 6, 2001

(54) TRANSPORT PROTEINS AND THEIR USES

(75) Inventors: Peter Francis Joseph O'Hare; Gillian Daphne Elliott, both of Oxted (GB)

(73) Assignee: Marie Curie Cancer Care, London (GB)

(*) Notice: Under 35 U.S.C. 154(b), the term of this patent shall be extended for 0 days.

This patent is subject to a terminal disclaimer.

(21) Appl. No.: 09/011,073

(22) PCT Filed: Jul. 25, 1996

(86) PCT No.: PCT/GB96/01831

§ 371 Date: Jan. 26, 1998

§ 102(e) Date: Jan. 26, 1998

(87) PCT Pub. No.: WO97/05265

PCT Pub. Date: Feb. 13, 1997

(30) Foreign Application Priority Data

Jul. 28, 1995 (GB) .................................................. 9515568
Jan. 26, 1996 (GB) .................................................. 9601570

(51) Int. Cl.⁷ ............................ C12N 15/87; C07K 14/03

(52) U.S. Cl. ....................... 435/455; 435/468; 435/471; 530/300; 530/350

(58) Field of Search .................................... 530/300, 350; 435/325, 243, 410, 455, 408, 471

(56) References Cited

FOREIGN PATENT DOCUMENTS 0 475 623 A1    3/1992    (EP) .
WO 97/04092    2/1997    (WO) .

OTHER PUBLICATIONS

Ngo et al, The Protein Folding Problem and Tertiary Structure Prediction, Mertz et al (eds), Birkhauser, Boston, 1994.*
Mercer et al., Wide type human p53 is antiproliferative in SV40–transformed hamster cells, Oncogene, vol. 5, pp. 973–980 (1990).
Shaw et al., Induction of apoptosis by wild–type p53 in human colon tumor–derived cell line, Proc. Natl. Acad. Sci., vol. 89, pp. 4495–4499 (1992).
Baker et al., Suppression of Human Colorectal Carcinoma Cells Growth by Wild–Type p53, Science, vol. 249, pp. 912–915 (1990).
Nicholson et al., "Localization of the herpes simplex virus type 1 major capsid protein VP5 to the cell nucleus requires the abundant scaffolding protein VP22a," Journal of General Virology, vol. 75, No. 5, pp. 1091–1099 (1994).
Elliott et al., "VP16 interacts via its activation domain with VP22, a tegument protein of herpes simplex virus, and is relocated to a novel macromolecular assembly in coexperessing cells," Journal of Virology, vol. 69(12), pp. 7932–7941 (1995).
Elliott & O'Hare, "Intercellular Trafficking and Protein Delivery by a Herpesvirus Structural Protein," Cell, vol. 88, pp. 223–233 (1997).
Leslie, J.et al., "Overexpression of the Herpes Simplex Virus Type 1 Tegument Protein VP22 Increases Its Incorporation into Virus Particles," Virology, 220:60–68, 1996.

* cited by examiner

Primary Examiner—Terry McKelvey
(74) Attorney, Agent, or Firm—Klarquist Sparkman Campbell Leigh & Whinston, LLP

(57) ABSTRACT

The present invention relates to transport proteins, in particular VP22 and homologues thereof, and to methods of delivering these proteins and any associated molecules to a target population of cells. This transport protein has applications in gene therapy and methods of targeting agents to cells where targeting at high efficiency is required.

8 Claims, 8 Drawing Sheets

Fig.4.
MTSRRSVKSGPREVPRDEYEDLYYTPSSGMASPDSPPDTSRRGALQTRSRQRGE
VRFVQYDESDYALYGGSSSEDDEHPEVPRTRRPVSGAVLSGPGPARAPPPPAGS
GGAGRTPTTAPRAPRTQRVATKAPAAPAAETTRGRKSAQPESAALPDAPASTAPT
RSKTPAQGLARKLHFSTAPPNPDAPWTPRVAGFNKRVFCAAVGRLAAMHARMAA
VQLWDMSRPRTDEDLNELLGITTIRVTVCEGKNLLQRANELVNPDVVQDVDAATAT
RGRSAASRPTERPRAPARSASRPRRPVE                          Δ267

Fig.5. (a)
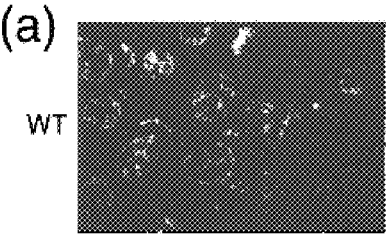
WT (b)
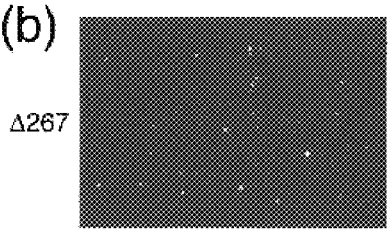
Δ267

(c) WT Δ267
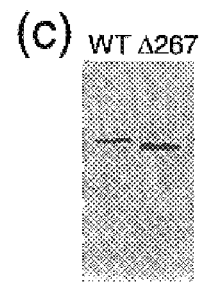

Fig. 6.
(a) 22-GFP
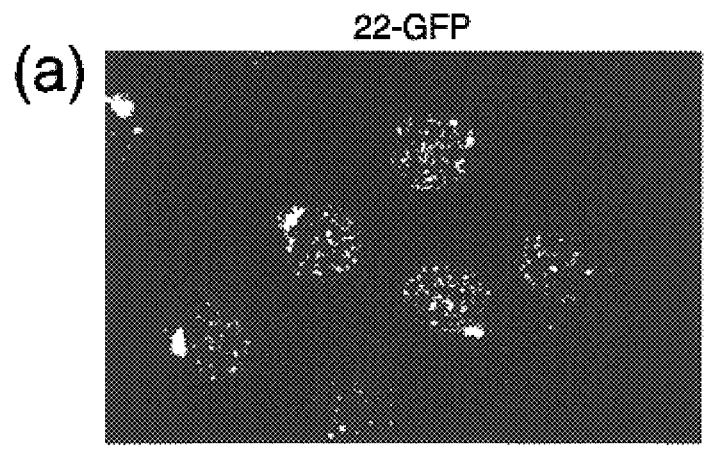
(b) 22-PEPTIDE
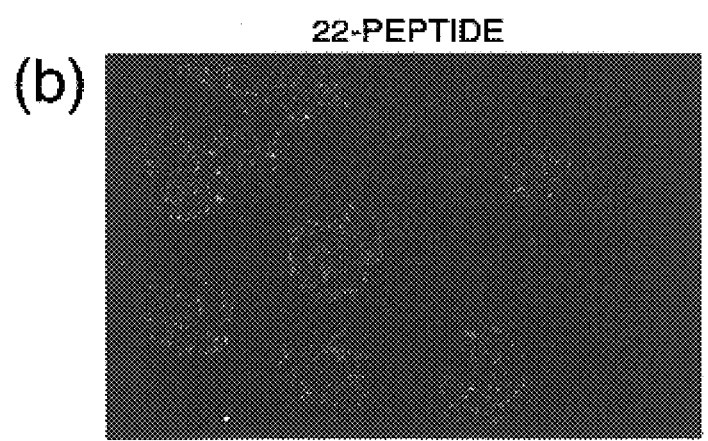
Fig. 7.
(a) β Gal   (b) VP22
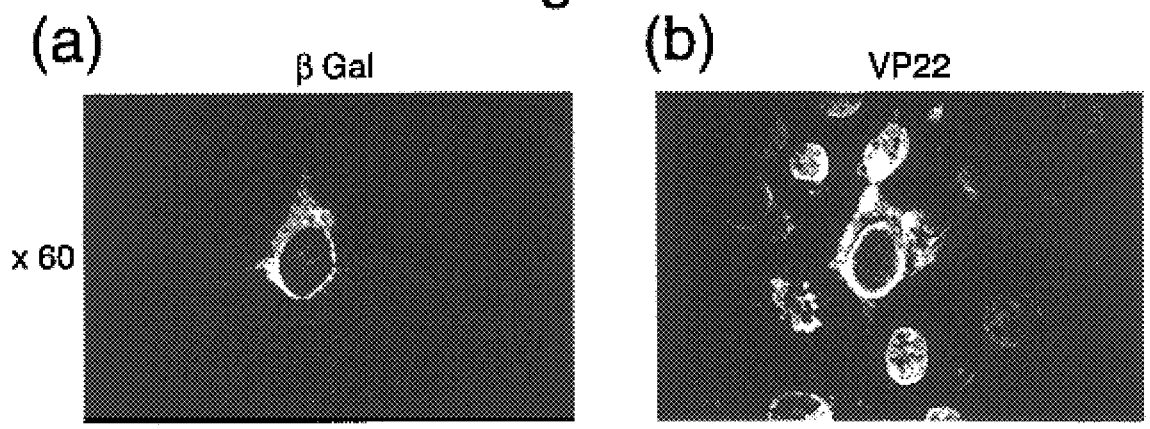
×60

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 301
      (B) TYPE: amino acid
      (C) STRANDEDNESS: single
      (D) TOPOLOGY: linear (xi) SEQUENCE DESCRIPTION: SEQ ID NO:1:

```
Met Thr Ser Arg Arg Ser Val Lys Ser Gly Pro Arg Glu Val
 1               5                  10
Pro Arg Asp Glu Tyr Glu Asp Leu Tyr Tyr Thr Pro Ser Ser
15                  20                  25
Gly Met Ala Ser Pro Asp Ser Pro Pro Asp Thr Ser Arg Arg
    30                  35                  40
Gly Ala Leu Gln Thr Arg Ser Arg Gln Arg Gly Glu Val Arg
        45                  50                  55
Phe Val Gln Tyr Asp Glu Ser Asp Tyr Ala Leu Tyr Gly Gly
            60                  65                  70
Ser Ser Ser Glu Asp Asp Glu His Pro Glu Val Pro Arg Thr
                75                  80
Arg Arg Pro Val Ser Gly Ala Val Leu Ser Gly Pro Gly Pro
85                  90                  95
Ala Arg Ala Pro Pro Pro Ala Gly Ser Gly Gly Ala Gly
    100                 105                 110
Arg Thr Pro Thr Thr Ala Pro Arg Ala Pro Arg Thr Gln Arg
        115                 120                 125
Val Ala Thr Lys Ala Pro Ala Ala Pro Ala Ala Glu Thr Thr
            130                 135                 140
Arg Gly Arg Lys Ser Ala Gln Pro Glu Ser Ala Ala Leu Pro
                145                 150
Asp Ala Pro Ala Ser Thr Ala Pro Thr Arg Ser Lys Thr Pro
155                 160                 165
Ala Gln Gly Leu Ala Arg Lys Leu His Phe Ser Thr Ala Pro
    170                 175                 180
Pro Asn Pro Asp Ala Pro Trp Thr Pro Arg Val Ala Gly Phe
        185                 190                 195
Asn Lys Arg Val Phe Cys Ala Ala Val Gly Arg Leu Ala Ala
            200                 205                 210
Met His Ala Arg Met Ala Ala Val Gln Leu Trp Asp Met Ser
                215                 220
Arg Pro Arg Thr Asp Glu Asp Leu Asn Glu Leu Leu Gly Ile
225                 230                 235
Thr Thr Ile Arg Val Thr Val Cys Glu Gly Lys Asn Leu Leu
    240                 245                 250
Gln Arg Ala Asn Glu Leu Val Asn Pro Asp Val Val Gln Asp
        255                 260                 265
Val Asp Ala Ala Thr Ala Thr Arg Gly Arg Ser Ala Ala Ser
            270                 275                 280
```

```
                                    -continued

Arg  Pro  Thr  Glu  Arg  Pro  Arg  Ala  Pro  Ala  Arg  Ser  Ala  Ser
                    285                      290

Arg  Pro  Arg  Arg  Pro  Val  Glu
295                      300

(2) INFORMATION FOR SEQ ID NO: 2:

(i) SEQUENCE CHARACTERISTICS:
        (A) LENGTH: 34
        (B) TYPE: amino acid
        (C) STRANDEDNESS: single
        (D) TOPOLOGY: linear (xi) SEQUENCE DESCRIPTION:  SEQ ID NO:2:

Asp  Ala  Ala  Thr  Ala  Thr  Arg  Gly  Arg  Ser  Ala  Ala  Ser
1                   5                        10

Arg  Pro  Thr  Glu  Arg  Pro  Arg  Ala  Pro  Ala  Arg  Ser  Ala  Ser
     15                       20                  25

Arg  Pro  Arg  Arg  Pro  Val  Glu
          30
```

TRANSPORT PROTEINS AND THEIR USES

This application is a §371 application of International Application No. PCT/GB96/01831, filed Jul. 25, 1996.

FIELD OF THE INVENTION

The present invention relates to transport proteins, and in particular to transport proteins based on VP22, homologues of VP22 or fragments thereof, to molecules and compositions including the transport proteins, and to methods of delivering these proteins and any associated molecules to a target population of cells, typically at high efficiency.

BACKGROUND TO THE INVENTION

The product of the herpes simplex virus type 1 (HSV-1) UL49 gene, the structural protein VP22 (4), is a major component of the HSV tegument, a compartment of the virion located outside the capsid and inside the envelope and composed of at least 10 or more additional virus polypeptides (for a review see (6)). VP22 has a molecular weight of 32 k, is very basic and is modified by phosphorylation and nucleotidylation (1,4,8,9,11) in the infected cell.

Despite being one of the major tegument proteins within the virion, together with the well characterised transcription regulatory protein VP16, little is known about the function of VP22 during the virus replicative cycle. It is not yet known if it is an essential virus protein, but it is possible that, in a manner similar to VP16, VP22 has two roles to perform during infection—initially as a functional protein during viral gene expression, and subsequently as a structural component of the virion during virus assembly. With regard to the former, some evidence exists to suggest that VP22 can bind specifically to HSV-1 DNA (2,8,10).

SUMMARY OF THE INVENTION

We recently demonstrated that there is a stable and specific interaction between VP16 and VP22, which has implications for the mechanisms of action of VP16 in assembly and transcriptional activation. During those studies, we found that when VP22 was in cells by itself it had an unusual pattern of behaviour. In the work described here, we extended these studies to investigate the cellular localisation in detail, and found that VP22 exhibits a highly unusual property in that it is efficiently transported from the cell in which it is originally expressed, and in which it displays cytoplasmic localisation, to adjacent cells within the monolayer, in which it is taken up into the nucleus. This pattern of behaviour has not been observed for any other of a range of proteins we have tested, eg VP16 and to our knowledge these properties and activities are unprecedented.

This unexpected property of VP22 was observed when, approximately 30 hours after introduction of either VP22 or VP16 into a cell monolayer, while VP16 could be detected on average in about 2–5% of the cells (as is conventional in such experiments), VP22 could be detected in nearly every cell of the monolayer. We further found specificity in VP22 intercellular transport and have demonstrated the involvement of a determinant at the C-terminal end of the protein. This comes from the result that a variant lacking the C-terminal 34 amino acids, while being expressed in a cytoplasmic location in initially expressing cells, was not transported to adjacent cells.

Protein secretion or export normally occur via specific pathways requiring well characterised signal sequences for sorting into the compartments and vesicles involved in export pathways for a review see (12). VP22 does not possess any conventional signal sequences and its route and mechanism of transport is highly unusual and is previously uncharacterised. Further studies on the determinants required within VP22 and of the physiological requirements within the cell should help clarify the pathway involved.

Thus, VP22, or more particularly the determinants involved in VP22 transport, could be transferred to other proteins to enable transport and efficient expression or uptake within a target cell population. Widespread utility and applications of this property can easily be envisaged.

Accordingly, the present invention is based on the above finding that it is possible to introduce into a first part of a target population of cells nucleic acid encoding a transport protein, and optionally with nucleic acid encoding proteins associated with the transport protein (eg as fusion partners), to express the nucleic acid, optionally from tissue specific promoters, to produce the protein(s), after which the transport protein is exported from the cells, together with any associated protein(s), to be taken up by a second part of the target population of cells not directly producing the protein (s). Typically, the protein(s) are found to be taken up by the second part of the population of cells at high efficiency, and tend to localise in the nuclei of the second part of the population of cells. Thus, the combination of initial introduction and subsequent transport allows the transport protein and any associated proteins to be delivered at high efficiency to the target population of cells.

Accordingly, in one aspect, the present invention provides a protein that is capable of being exported from the cells in which it is expressed and is capable of being taken up in other cells, for example those not directly producing the protein. Preferably, the transport protein is associated with one or more other proteins whose delivery to the populations of cells is desired.

Further experiments have confirmed that VP22 is imported into cells when it is added as an extract to the extracellular medium. This confirms that it is not necessary for the VP22 to be expressed in at least a part of the population of cells for the observed intercellular transport to occur.

In one alternative aspect, the VP22 transport protein can be coupled to the associated molecules, eg covalently, or incorporated with associated molecules, and used in that form, as opposed to the use of an expression vector to produce the protein and/or the associated molecule. In particular, this could allow non-peptidyl molecules, such as nucleic acid, drugs or markers (in addition to or as alternatives to proteins) to be associated to the transport protein, and be taken up into a population of cells, without the need to express the VP22 and the associated molecule in at least a part of the population of cells to which delivery of the VP22 and/or the associated molecule is desired.

In a preferred embodiment, the present invention provides a transport protein which is:

(i) VP22 or an active portion thereof;
(ii) a fragment or homologue of VP22 including one or more of the determinants providing the transport property; or,
(iii) a fragment from the C-terminal 34 amino acids of VP22;

the transport protein being optionally associated with one or more other molecules whose transport to the target population of cells is desired.

In this invention, "an active portion" means a peptide which is less than full length VP22, but which retains the property of being secreted by the cells producing it and of being taken up other cells.

In a further aspect, the present invention provides a composition comprising one or more of the above transport proteins, the proteins being optionally associated with one or more molecules whose delivery to a population of cells is desired.

In a further aspect, the present invention provides a method of transporting a desired molecule into a population of cells by exposing the cells to the desired molecule and the transport protein as set out above.

Thus, in this aspect, the invention provides a method which avoids the need initially to transfect the population of cells with nucleic acid encoding the transport protein and optionally the desired molecule. Thus, this can also allow the transport of molecules which are non-peptidyl, which could not be expressed in a cell, as the desired molecule and the transport protein can be added to the the medium surrounding the cells.

In some embodiments, the desired molecule can be coupled covalently to the transport protein and these entities exposed to the target population of cells. Alternatively, the desired molecule and the transport protein can be non-covalently associated, eg using lipid based vehicles incorporating a desired molecule such as nucleic acid and the transport protein.

Accordingly, in a further aspect, the present invention provides a method of preparing a composition including a desired molecule for transport to a target population of cells comprising covalently or non-covalently associating the desired molecule and transport protein.

In a further aspect, the present invention provides nucleic acid encoding the transport protein and (optionally) the associated molecules. For example, in embodiments in which the transport protein is expressed as a fusion construct, the nucleic acid can be provided which encodes the transport protein and its fusion partner(s).

In a further aspect, the present invention provides expression vectors incorporating nucleic acid encoding the transport protein or an active portion or fragment thereof, and optionally nucleic acid encoding the associated molecules.

In a further aspect, the present invention provides host cells transfected with the above expression vectors.

In a further aspect, the present invention provides a method of transporting a desired protein or peptide to a target population of cells, the method comprising:

(i) transfecting, infecting or otherwise introducing into a first part of a target population of cells with nucleic acid encoding a transport protein, and optionally with nucleic acid encoding proteins associated with the transport protein;

(ii) expressing the nucleic acid to produce the protein(s), after which the transport protein is exported from the cells, together with any other proteins associated with it, to be taken up by a second part of the target population of cells not directly producing the protein(s).

It will be appreciated that introduction or transfection of a first part of a target population of cells could be achieved by infecting with a recombinant virus.

In a further aspect, the present invention provides a method of transporting a desired molecule into a population of cells comprising:

(I) coupling the desired molecule to a transport protein to form a complex; and, (ii) exposing the cells to the complex so that the cells can take up the complex.

In this method, the desired molecule, which may be non-peptidyl, can be coupled to, e.g. covalently or incorporated with, the transport protein.

In a further aspect, the present invention provides the above transport proteins and vectors for use in methods of transporting molecules, both in research methods and in methods of therapy. The present invention is particularly applicable in methods of targeting agents to populations of cells where targeting at high efficiency is required, eg in gene therapy techniques, the treatment of cancer, eg by the delivery of tumour suppressing agents to cells.

BRIEF DESCRIPTION OF THE DRAWINGS

FIG. 4 shows the protein coding sequence of VP22 (SEQ ID NO:1), the product of the HSV-1 UL49 gene showing the truncation point for the Δ267 mutant which deletes residues 268–301 (SEQ ID NO:2);

FIGS. 5(a)–5(b) show the results of immunofluorescence carried out after full length VP22 and Δ267 VP22 containing extracts were added to the extracellular medium; and, FIG. 5(c) shows a Western blot of the full length VP22 and Δ267 VP22 cellular extracts;

FIGS. 6(a)–6(b) show the import of VP22 or modifications thereof when applied to medium.

FIG. 7(a) shows a typical picture of a field with one microinjected cell stained with an antibody to β-gal.

FIG. 7(b) shows the same field of cells where VP22 is seen not only in the microinjected cells, but in numerous surrounding cells;

DETAILED DESCRIPTION

Materials and Methods

Figure 1:
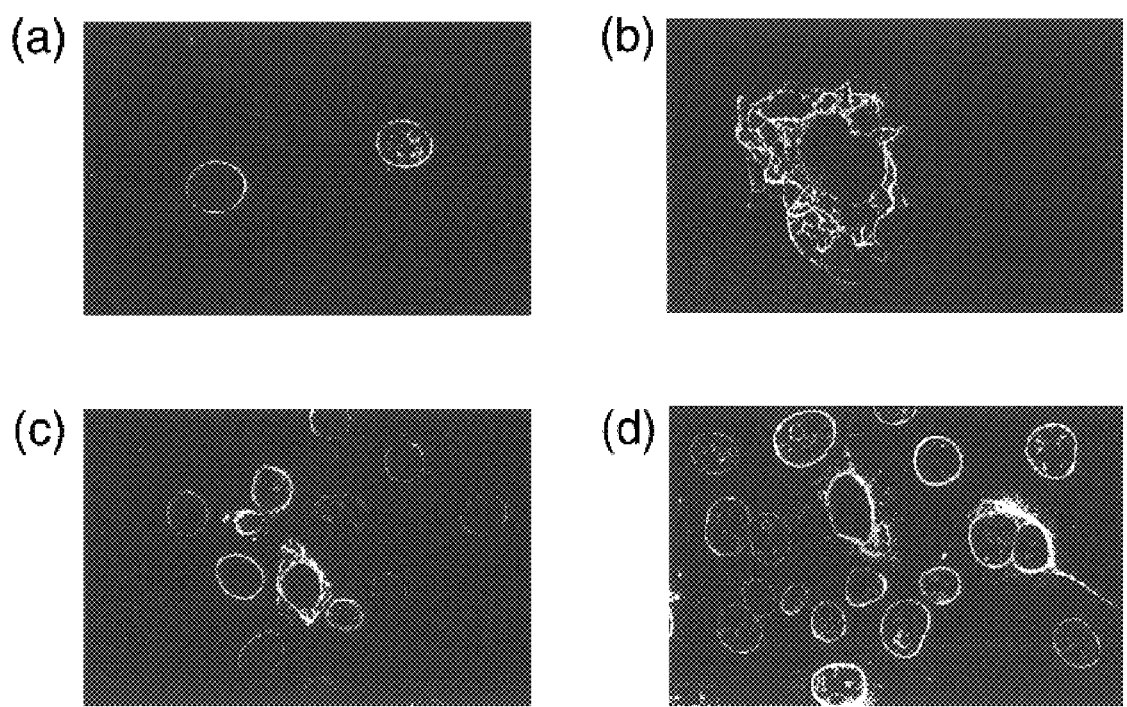
FIGS. 1(a)–1(d) show the immunofluorescence of COS-1 cells expressing VP22. COS-1 cells grown on coverslips were transfected with the VP22 expression vector. Forty hours after transfection the cells were fixed in 100% methanol for 15 mins at room temperature and incubated with the anti-VP22 monoclonal antibody P43, followed by an FITC-conjugated secondary antibody. The cells were then analysed using confocal microscopy. (a) Typical nuclear localisation exhibited by VP22 expressing cells. (b) Cytoplasmic pattern of VP22 expression present in about 5–10% of expressing cells. (c) Pattern of VP22 localisation observed when the levels of expression are increased. (d) VP22 expression resulting in the protein being localised in every cell within the monolayer.

Cells and Viruses.

HeLa cells (human epithelial carcinoma cells), COS-1 cells (monkey kidney fibroblasts transformed by SV40 T-antigen), Vero cells (monkey kidney fibroblasts) and BHK (baby hamster cells) were grown in Dulbecco's modified minimal essential medium containing 10% newborn calf serum.

Plasmids.

The eukaryotic expression vector pGE109 contains the VP22 open reading frames, under the control of the hCMV IE promoter, and has been described previously (4). Briefly, the expression construct was made by using the polymerase chain reaction to amplify the VP22 open reading frame with linkers containing BglII or BamHI restriction enzyme sites, to facilitate subsequent introduction into a vector under the control of the hCMV enhancer/promoter region.

Antibodies.

These experiments used anti-VP16 monoclonal antibody LP1 and anti-VP22 monoclonal antibody p43. The p43 antibody resulted from immunisation of mice with a preparation of virion proteins from herpes simplex virus. A polyclonal antibody (AGV30) reactive against VP22 was produced by immunisation of rabbits with a fusion protein consisting of glutathione-S-transferase linked to the VP22 open reading frame. The fusion protein was created by in frame insertion of a Bgl II-BamHI fragment from pGE109 into the BamHI site of the commercially available (Pharmacia) bacterial expression vector pGEX2T to create the vector pGST-VP22. E. coli strain HB101 containing pGST-VP22 were induced by addition of IPTG (0.1 mM) to a logarithmic phase culture, and the cells harvested 3 hours later. After pelleting, the cells were resuspended in phosphate buffered saline containing 0.5% NP-40, sonicated using a Branson Ultrasonic cell homogeniser and clarified by centrifugation at 12000 rpm for 20 minutes at 4 degrees C. The GST-VP22 fusion protein was then purified by affinity chromatography on glutathione Sepharose beads (Pharmacia), washing of unbound protein in PBS 0.5% NP40 and elution in 10 mM Tris-HCl buffer (pH 8.0) containing 5 mM glutathione. The fusion protein was injected (approx. 50 μg per injection) in adjuvant at 4-weekly intervals into each of three rabbits and sera harvested after a total of 17 weeks.

SDS-PAGE and Western Blotting.

Proteins were separated by electrophoresis through SDS-polyacrylamide gels crosslinked with bis-acrylamide. Gels containing radiolabelled samples were dried and exposed to X-ray film. Gels for Western blotting were transferred to nitrocellulose filters and reacted with the appropriate antibody. A horseradish peroxidase linked secondary conjugate was used, with reactive bands being visualised by development with 3, 3' diaminobenzidine tetrahydrochloride dihydrate (DAB) or with enhanced chemiluminescence.

Transfections and Immunofluorescence.

The day before transfection cells were plated into 6 well trays (6×35 mm) containing one coverslip per well, at a density of $2 \times 10^5$ cells per well. DNA transfections were carried out with 500 ng expression plasmid made up to 2 μg with pUC19 DNA, using the calcium phosphate precipitation technique modified with BES [N,N-bis(2-hydroxyethyl)-2-aminoethanesulfonic acid] buffered saline in place of HEPES-buffered saline previously described (3,5). Cells were fixed 40 hrs after transfection in 100% methanol for 15 mins at RT, then washed in phosphate buffered saline (PBS). For transfections, the cells on coverslips were blocked by incubation with PBS/10% calf serum for 15 mins at RT. Primary antibody was added in the same solution (p43 at a dilution of 1:100,) and incubated for 20 mins at RT. Following extensive washing with PBS, secondary antibodies (FITC-conjugated anti-mouse IgM and/or Texas Red-conjugated anti-rabbit IgG) were added in PBS/10% calf serum and incubated for 10 mins. Extensive washing was again carried out in PBS before the coverslips were mounted in glycerol and examined in dual channels using a Biorad MRC600 confocal microscope. Phase contrast pictures were photographed using standard light microscope.

Results

VP22 Localises in Two Distinct Patterns.

The cellular localisation of VP22 was investigated by immunofluorescence of VP22 expressing cells using the anti-VP22 monoclonal P43, followed by confocal microscopy. COS cells were transfected as described above, and the cells fixed 30 to 40 hours later in methanol and processed for detection of VP22. Initial results demonstrated that, in the majority of VP22 containing cells, the protein was present in a distinctive nuclear pattern, frequently showing enrichment around the nuclear rim. FIG. 1a illustrates typical examples of the nuclear patterns of VP22. However in a number of cells VP22 was present in a very different cytoplasmic filamentous pattern (FIG. 1b). In this case, the protein was detected in a meshwork or cage like pattern within the cytoplasm and was excluded from the nucleus. This heterogeneity in distribution, although not by itself unusual, was not observed with the other HSV tegument protein under study (VP16), which exhibited a pattern differing little from cell to cell and consisted mainly of a diffuse cytoplasmic pattern with minor amounts present in the nuclei.

Further examination revealed that the cytoplasmic versus nuclear distribution of VP22 was not random with respect to each other, ie one in which a central cell containing cytoplasmic VP22 was surrounded by a halo of cells containing nuclear VP22, where the protein was clearly enriched in the region of these latter cells adjacent to the central cell containing the cytoplasmic VP22 (FIG. 1c). Finally, the areas of the monolayer in which VP22 could be detected in every cell again displayed this distribution with the cytoplasmic pattern being observed in a minority of cells, with a nuclear pattern in the surrounding cells (FIG. 1d).

Figure 2:
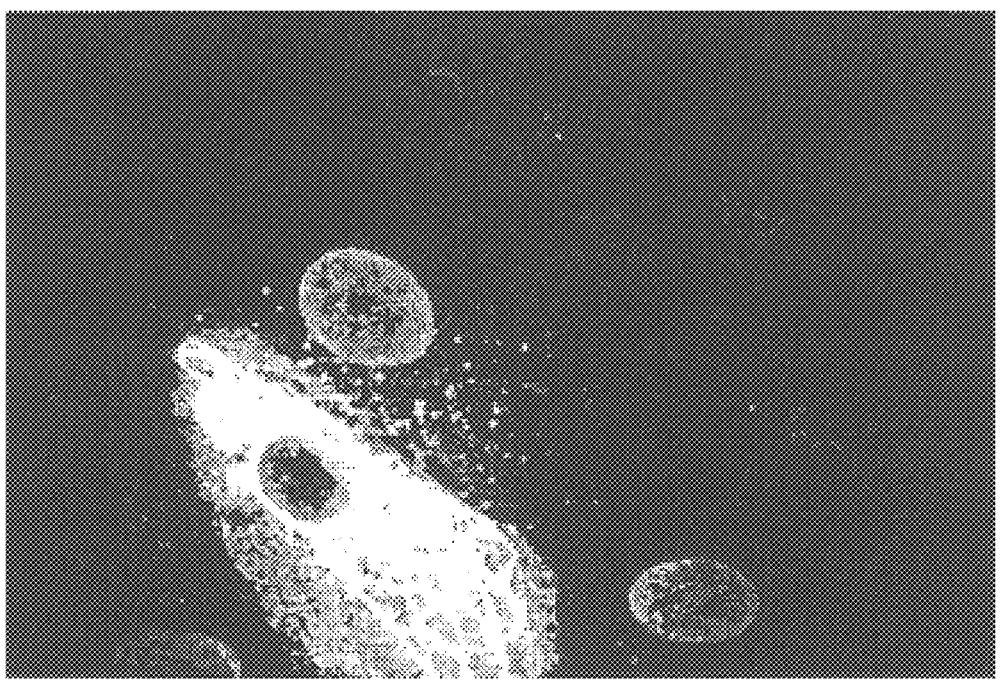
FIG. 2 shows VP22 transport in Vero cells. Transfection and detection were performed as for FIG. 1 except that the experiment was performed in Vero cells. The field shows a foci of VP22 in a central cell where it is cytoplasmic and in a gradient of intensity in surrounding cells where it is localised to the nucleus.

Initially, these experiments were performed in COS cells which by virtue of the SV40T-antigen allow replication of the VP22 expression plasmid used here. Although we did not detect this type of distribution with other proteins (e.g. VP16 see above) which were expressed from identical vectors, we wished to rule out the possibility that the pattern of VP22 distribution was related to the use of COS cells. Similar experiments were therefore performed with Vero cells and HeLa cells and identical results were obtained. FIG. 2 shows expression of VP22 in Vero cells in the pattern described above in which a central cell containing cytoplasmic VP22 is surrounded by cells containing nuclear VP22. In this case, VP22 is seen in a gradient of decreasing intensity, from the central cell to the adjacent cells with intense nuclear VP22, to cells further away with less intense nuclear VP22.

Figure 3:
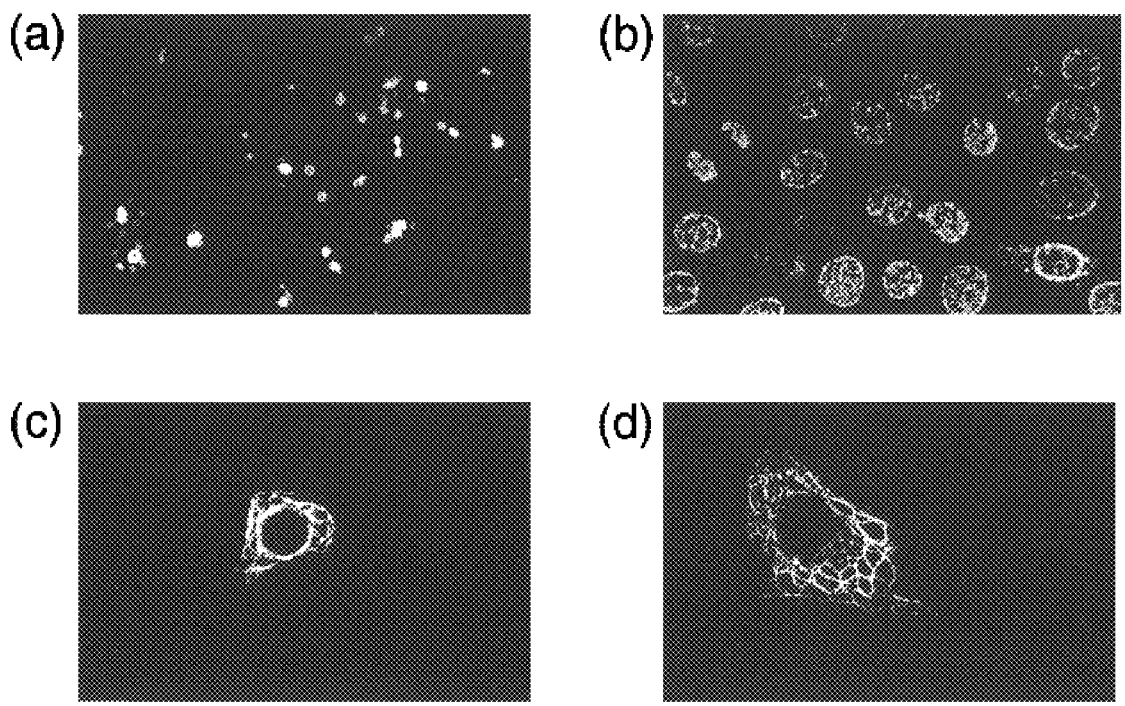
FIGS. 3(a)–3(d) show a transfection time-course of VP22 expression demonstrates that VP22 is transported between cells. COS-1 cells were transfected and fixed at 14, 20, 26, and 38 hrs post-transfection. The confocal images shown are for the 20 hr time point at 20× magnification (panel a) and 38 hr at 100× magnification (panel b).

These surprising results indicate that VP22 was being transported from the cells in which it was initially being synthesised and was present in a cytoplasmic pattern, to adjacent cells and also to cells further removed again, where it localised to the nucleus. To demonstrate VP22 moving between cells, a time course of transfection was carried out. By 14 hours after transfection, it was possible to detect VP22 expression in individual cells. At 20 hrs, foci of cells containing VP22 could be seen wherein a central cell containing intense VP22 was surrounded by several cells containing less intense VP22 (FIG. 3a, lower magnification to facilitate point), while by 38 hrs virtually every single cell contained the protein (FIG. 3b).

As an additional piece of evidence that VP22 was being transported between cells, two separate dishes of COS-1 cells were transfected with either the VP22 expression vector, and pRG50, a VP16 expression vector. Twenty-four hours later, each dish was trypsinised and the two populations mixed and plated onto coverslips. Twenty-four hours later, it was possible to detect VP16 expressing cells which also contained VP22 within the nucleus, demonstrating that cells which had never been exposed to the VP22 expression vector had taken up the VP22 protein.

Intercellular Transport Requires a C-terminal Determinant within VP22.

To begin characterisation of the requirements within VP22, we tested a series of variants containing short (3–4 amino acids) in frame insertions and a deletion mutant lacking SEQ ID NO:2, which is residues 267 to the end (residue 301) of the protein. The insertion mutants contained insertion at position 60, 159, 192 and 267. None of the insertion mutants Ins 60, Ins 159 or Ins 267 had any effect on the pattern of localisation of VP22 or its ability to undergo intercellular transport (data not shown, all the same as wild type). The insertion at position 192 did however have a significant effect. This mutant exhibited a pattern of distribution similar to the cytoplasmic distribution seen with the wild type; thus, nuclear staining in adjacent cells was not observed, fewer positive cells were observed overall and in VP22 positive cells, the pattern was exclusively cytoplasmic (FIG. 3c).

An identical phenotype was observed for the deletion mutant lacking the C-terminal 34 residues 267–301 (FIG. 3d). Note that the insertion mutant at position 267 was normal. The pattern of distribution showing exclusively cytoplasmic VP22 and lack of transport to surrounding cells for deletion mutant 267–301 and insertion mutant 192 was not due to inefficient synthesis. When total synthesis was compared by Western blotting, similar amounts of the w/t and mutant proteins were observed.

To begin to address the possibility that this property of intercellular transport could be utilised for the transport of additional peptides or proteins, we tested whether a variant of VP22 (VP22ep) which contained a 12 residue extension on its C-terminal end (containing a recognition site for a monoclonal antibody), would also be transported. The results demonstrated efficient transport of the extended protein. In fact, FIG. 3b, which demonstrates transport in Vero cells, utilised this C-terminal extended variant. As indicated above, a foci of cells containing central cytoplasmic VP22ep was surrounded by cells containing nuclear VP22ep and, as for w/t protein, expression of VP22 could be detected in virtually every cell in the monolayer. Moreover, the protein which was being detected was indeed the fusion protein, and not some fortuitous deletion product, since it could be detected using either the anti-VP22 antibody p43 or the antibody to the C-terminal peptide extension. This important result demonstrates that it is indeed feasible to promote the delivery of peptides or proteins to cells by linking them to a suitable transport protein such as VP22.

Those skilled in the art could routinely employ these or other site-directed mutagenesis methodologies to map or refine the determinants in VP22 that are critical and/or important for the transport property, thereby allowing the use of fragments of VP22, rather than the full length protein.

VP22 Uptake from Medium.

Although VP22 was readily detected on the cell surface, we have as yet been unable to detect VP22 in the medium of transfected cells. However to examine the ability of VP22 to be imported from the extracellular medium, a soluble extract made from VP22-expressing cells was added to the media of untransfected cells. VP22 was imported and was localised to the nucleus with high efficiency and rapidly (see FIG. 5(a)), uptake occurring within 5 mins after addition to media (possibly explaining our inability to detect it in the medium). The uptake mechanism was not affected by incubation at 4° C. suggesting that internalisation was not via normal endocytosis. In control experiments uptake from the medium was not observed for any other protein we have tested.

Soluble extracts containing either full-length (WT), or truncated (Δ267) VP22 were added to the media covering COS-1 cells grown on coverslips, and the cells fixed 1 hr later. Equal amounts of the extracts were also analysed by SDS-PAGE and Western blotting.

To make the soluble extract, one million COS-1 cells were transfected with either full-length or Δ267 VP22 expression vectors, harvested 36 hrs later, and the extract made in 10 mM HEPES (pH 7.9), 400 mM NaCl, 0.1 mM EDTA, 0.5 mM DTT and 5% glycerol. Half of the extracts were then added to the media covering $5 \times 10^5$ COS-1 cells grown on coverslips, the cells fixed 1 hr later, and immunofluorescence carried out using the polyclonal anti-VP22 antibody (see FIGS. 5(a) and 5(b)). One tenth of the extract described was analysed by electrophoresis on a 10% acrylamide gel followed by Western blotting using monoclonal antibody P43 (see FIG. 5(c)).

Furthermore, the VP22 deletion mutant Δ267, while present in the soluble extract in equivalent amounts to full-length (see FIG. 5(c), Δ267), was not detected intercellularly indicating a requirement for the C-terminal 34 residues for this process (FIG. 5(b)).

To investigate this further, we have made a peptide corresponding to the C-terminal 34 residues (shown in SEQ ID NO:2) and added a 12 residue tag to allow immunological detection. This peptide, when applied to cell media, gains entry to the cell and is transported to the nucleus (FIG. 6b). These experiment shows that these C-terminal 34 residues are a) required and b) sufficient to give transport.

Transport of Fusion Proteins

Although, as indicated above, we have demonstrated that peptides can be transported by fusion to VP22 it was unknown how big a protein could be fused to VP22 to facilitate transport.

COS-1 cells in 6 mm dishes were transfected with plasmids pGE109, Δ267 or VP22-GFP which had been constructed by insertion of the UL49 open frame reading frame into the BamH1 site of the plasmid pGFP-N1 (Clontech), resulting in a fusion of VP22 to the N-terminus of green fluorescent protein (GFP). 40 hrs after transfection the cells were harvested and high salt extracts were prepared. Western blotting of these extracts demonstrated that while there were equivalent amounts of the full length and Δ267 variants of VP22 present in the extracts, the level of 22-GFP protein was about 5-fold less. Equal volumes of each extract was added to the media covering the COS-1 cells on coverslips, left for 1 hour, then fixed in 100% methanol. Immunofluorescence was carried out using AGV30. The results showed (FIG. 6a) that the VP22-GFP fusion protein could be detected in the recipient cells and that it had accumulated in the nuclei.

In summary, we have shown that we can make extracts of cells expressing a fusion protein where the attached protein was 32 Kda, and after applying the extract to cell medium, we can detect the fusion protein in the nuclei.

Microinjection of VP22

Although transport by transfection is valuable for tissue culture uses, it may not be a really a valid route for delivery in tissues or patients.

Microinjection (and also liposome delivery) are utilised in vivo and it is additionally useful to demonstrate VP22 transport by a route of delivery which could have in vivo utility.

cos-1 cells plated onto coverslips were microinjected with a mixture of 100 ng/μl pGE109 and 100 ng/μl pBAG as a marker for the injected cell(PNAS 84: 156–160), using a Carl Zeiss semi-automatic microinjector in manual mode. The cells were incubated for 24 hrs, fixed in 100% methanol, and double-immunofluorescence using the polyclonal anti-VP22 antibody AGV30 (1:500) and monoclonal anti-β galactosidase (1:50) (Promega). FIG. 7a shows a typical picture of a field with one microinjected cell, stained by antibody to β-gal. In the same field of cells, VP22 (FIG. 7b) is seen not only in the microinjected cells, but in numerous non-injected cells. Thus, this route of delivery could be used in vivo by microinjection into e.g. the centre of tumours, to deliver VP22 or a variant thereof. Other routes of delivery would, of course, be equally viable, this just demonstrates one route directly. Currently two main routes of delivery of genes are utilised, namely liposome-mediated and virus infection. Therefore, the gene for VP22 or various modifications including fusion proteins, could be incorporated into liposome vesicles for in vivo delivery. Likewise, liposome delivery is also utilised in tissue culture systems. Alternatively, the gene for VP22 or varients could be inserted into the genomes of e.g. adenovirus or retroviruses for delivery of infection. In both cases expression would be in the initial population of transfected or infected cells, but VP22 would be delivered to surrounding cells. This is particularly useful where delivery is by disabled virus vectors which are designed not to replicate. Delivery in this case would be enhanced. Direct microinjection of the genes or direct application of the naked DNA are also routes currently being explored in the field.

Transport of VP22 into Different Cell Types

We have further demonstrated that VP22 can be transported into a different cell type from the one in which it is initially expressed.

COS-1 cells in a 60 mm plate were transfected with 1 μg pGE109 made up to 4 μg with PUC19 DNA. 24 hrs after transfection the cells were removed by trypsinization and mixed with previously trypsinized BHK-21 cells (hamster) at a ratio of 1:20. The mixture of cells was plated onto coverslips in 6 well plates and incubated for a further 20 hrs, following which they were fixed in 100% methanol. Double immunofluorescence was carried out using AGV30 (1:500) and the monoclonal anti-T antigen pAB419 (neat) to identify the COS-1 cells (J. Virol. 39:861–869).

Figure 8:
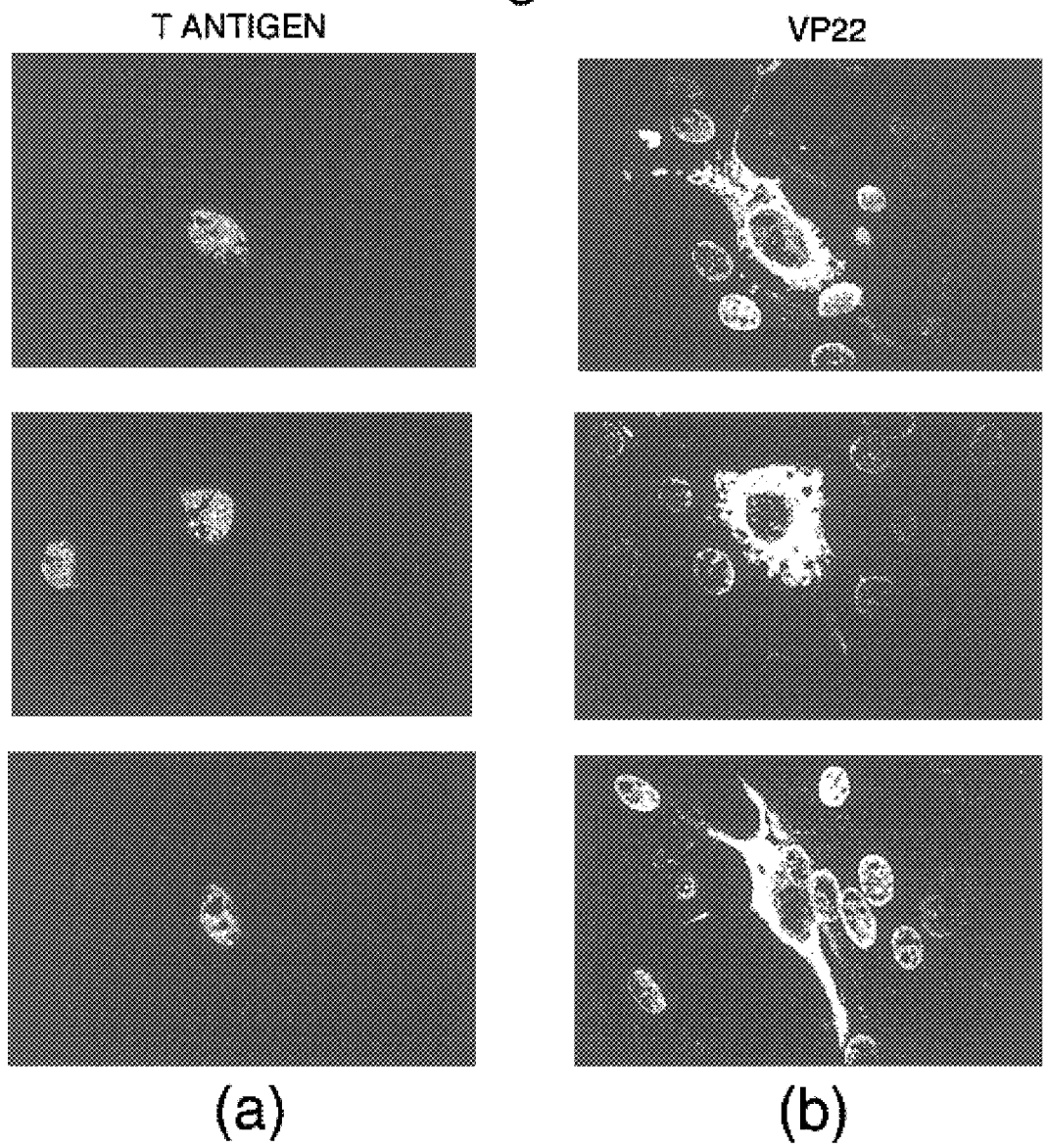
FIG. 8(a) shows typical fields of mixed cells marked by T-antigen positive COS cell. The surrounding BHK cells are not detected by the T-antigen antibody.
FIG. 8(b) shows the VP22 positive cells, i.e. the central COS cell plus the surrounding non-transfected BHK cells are seen.

FIG. 8 shows a typical field of mixed cells where the T-antigen positive COS cells are seen (FIG. 6a, left hand panel), (the surrounding BHK cells of course are not detected by the T-antigen antibody), and in FIG. 8b, right hand panel the VP22 positive cells, i.e. the central COS cell plus the surrounding non-transfected BHK cells are seen.

DNA Binding Properties of VP22

We have shown that in cells where VP22 is nuclear, it binds to the condensing chromosomes during mitosis. This shows a strong association with the chromosomes during mitosis and demonstrates that once VP22, or variants is taken up into the cell, they will also be passed onto the daughter cells after division. This property makes VP22 additionally useful for delivery. Moreover we have shown that in vitro, VP22 has non-specific DNA binding properties probably explaining (at least in part) the in vivo chromatin association. These two observations combined add to the potential of VP22 to bind DNA and to deliver DNA/genes to nuclei.

Figure 9:
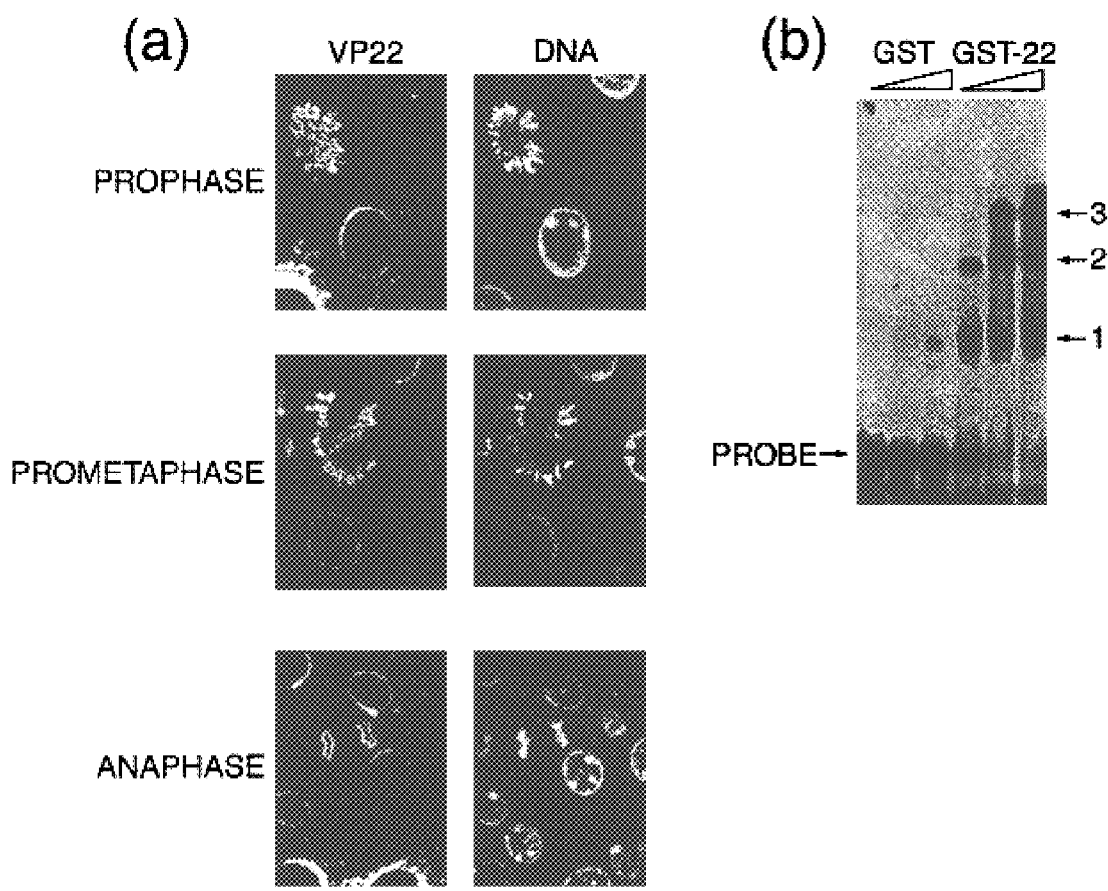
FIG. 9(a) shows Cos-1 cells expressing full-length VP22 were stained for both VP22 and DNA, and cells at different stages of mitosis analysed. To stain DNA propidium iodide was added to the glycerol mountant at a final concentration of 3 μg/ml. Cells representing prophase, prometaphase and anaphase are shown.
FIG. 9(b) shows increasing amounts of GST and GST-VP22 fusion protein were incubated with an end-labelled 40bp oligonucleotide (T24), and resulting complexes analysed by gel-shift assay. The VP22-specific complexes are labelled 1 to 3.

During the analysis we observed that a proportion of the cells with nuclear VP22 contained the protein in a pattern similar to that of mitotic chromatin. Double staining of cells for both VP22 and DNA revealed that cells at all stages of mitosis could be detected with VP22 localised around the condensed chromosomes (FIG. 9a). To determine if VP22 could interact directly with DNA, we tested the ability of a GST-VP22 fusion protein to bind a 40 bp oligonucleotide probe, by gel retardation assay. Dose-dependent increase in the appearance of 3 complexes (FIG. 9b), not present in the GST controls, was observed for GST-VP22. The complexes of increasing size may represent multimerization of the protein, since the largest one formed less efficiently on shorter probes (not shown). Moreover VP22 was capable of binding to a range of DNA probes suggesting that the protein interacts with DNA in a non-specific manner.

VP22 Transport in Virus Infected Cells

One of the main routes of gene delivery for gene therapy is via the use of viruses. Typically such viruses are disabled in some way so that they will replicate inefficiently or not at all. The desire is that limiting replication will prevent complications due to pathogenesis. Safety of virus vectors is a major issue in gene therapy and much effort is going into developing stringently disabled viruses. But the disadvantage of using disabled viruses is that the genes of interest are then delivered only to those initially infected cells.

We wished to demonstrate directly that VP22 could be transported from a virally infected cell to a non-infected cell. To this end we infected cells with a disabled herpes simplex virus mutant HSV-1 [gH-ve]. This virus lacks the gene for an essential virus glycoprotein, gH, and must be propagated on a specialised complementing cell line containing gH. But when this virus infects non-complementing cells (ie any cell type not containing the virus gH), the virus can penetrate an initial population of cells, synthesis virus proteins (except gH), and assemble virus particles, but these are non-infectious. No second round of infection occurs. We wished to demonstrate that VP22 could be transported form a cell initially infected with the HSV-1 [gH-ve] virus mutant (Desai, P. J. et al. J Gen Virol 69 (Pt 6): 1147–56 (1988); Forrester, A. et al. J Virol 66: 341–8 (1992) U. Gompels & A. Minson Virology 153: 230–47 (1986)).

Figure 10:
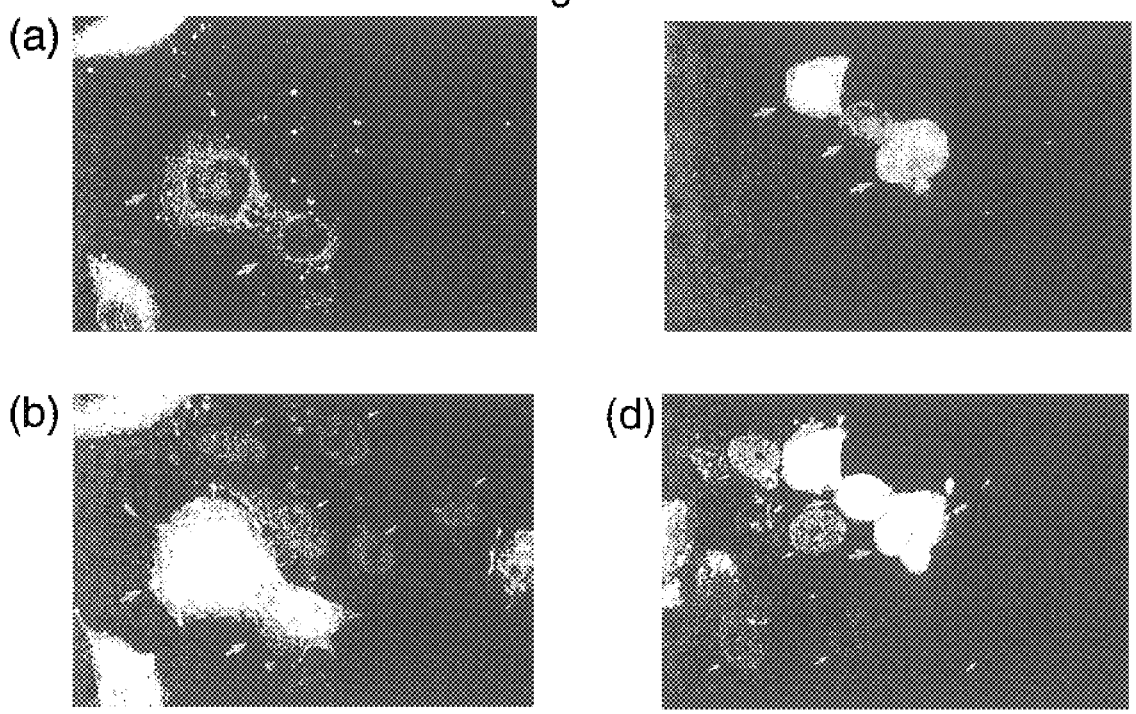
FIGS. 10(a)–10(d) show vero cells infected with HSV-1 [gH-ve]. a shows a field 24 hour after infection stained for beta-galactosidase. b shows the same field stained for VP22. c shows a field 66 hour after infection stained for beta-galactosidase. d shows the same field stained for VP22.

Vero cells were infected with HSV-1 [gH-ve] at a multiplicity of approximately 0.2 pfu/cell. Therefore roughly 1 in 5 cells would be initially infected. Twenty four or sixty six hours after infection the cells were fixed in methanol and assessed for the presence of VP22, or beta galactosidase. Note that this virus contains the gene for beta-galactosidase and the presence of beta-galactosidase serves as a marker for the primary infected cell. The results are shown in FIG. 10.

FIG. 10a shows a field 24 hour after infection stained for beta-galactosidase.

FIG. 10b shows the same field stained for VP22.

FIG. 10c shows a field 66 hour after infection stained for beta-galactosidase.

FIG. 10d shows the same field stained for VP22.

In FIG. 10a two cells expressing beta-galactosidase are arrowed. Note the surrounding cells lacking beta-galactosidase. In the same field stained for VP22 (FIG. 10), these two cells are also VP22 positive (large arrowheads), but in addition several surrounding cells are detected containing VP22 (small arrowheads), which were beta-galactosidase negative.

Again in FIG. 10c (66 hours post infection) three cells are shown which are beta-galactosidase positive (large arrowheads). In the same field stained for VP22 (FIG. 10d), these same three cells are positive but in addition surrounding cells, beta-galactosidase negative and therefore non-infected, nonetheless contain VP22 which has accumulated in the nuclei (small arrowheads). Note these latter cells completely lack detectable beta-galactosidase, despite the intense staining in the three central positive cells.

The results demonstrate that VP22 can be transported from virally infected cells. This is not property of only herpes virus infection since VP22 can be transported from transfected or microinjected cells. Thus transport does not require any other herpes virus encoded protein and will almost certainly occur utilising any virus vector such as adenovirus or retroviruses.

Therefore we have directly demonstrated proof of principle for VP22 transport from virus infected cells. It is easily envisioned that fusion proteins containing a gene of interest could be constructed linked to the gene for VP22, or the active portion thereof, and inserted into virus vectors under the control of a constitutively efficient or tissue-specific promoter. The fusion protein will then be delivered to a much greater population than those initially infected.

Discussion

The above results demonstrate that VP22 exhibits a highly unusual property in that it is efficiently transported from the cells in which it is originally expressed, and in which it displays cytoplasmic localisation, to adjacent cells within a cell the monolayer, where it is taken up into the nucleus. This pattern of behaviour has not been observed for any other of a range of proteins we have tested and we can find no previous demonstration of this activity. Thus, for example, VP16 is also expressed in the cytoplasm of cells, but its pattern of expression is completely homogeneous within the population of expressing cells and it is not transported to adjacent cells. This difference and the unexpected property of VP22 is shown from the result that approximately 30 hours after introduction of either VP22 or VP16 into a cell monolayer, while VP16 can be detected on average in about 2–5% of the cells, VP22 can be detected in every cell of the monolayer.

This work also demonstrates the specificity in VP22 intercellular transport and demonstrates the involvement of a determinant at the C-terminal end of the protein since a variant lacking the C-terminal 34 amino acids, while being expressed in a cytoplasmic location in initially expressing cells, is not transported to adjacent cells. The experiments show intercellular transport of VP22 in a number of different cell types including COS-1 cells, Vero cells, and HeLa cells, ie the phenomenon does not appear to be specific to the COS cells in which it was initially observed.

Protein secretion or export normally occur via specific pathways requiring well characterised signal sequences for sorting into the compartments and vesicles involved in export pathways. In one of the main mechanisms of protein secretion, signal sequences usually residing in the extreme N-terminus of a protein, are recognised by a complex of a 7S RNA and at least 6 polypeptides which together comprise the signal recognition particle (SRP). Recognition by the SRP is followed by docking and transfer of the signal peptide to a receptor within the endoplasmic membrane. The emerging polypeptide is then discharged across the ER membrane and subsequently processed through a complex network of interactions and vesicle assembly in the Golgi network. VP22 does not possess any conventional signal sequence and its pattern of distribution within the cytoplasm does not resemble ER or Golgi distributions.

There have been a small number of previous examples of mammalian protein secretion by non-classical pathway(s), including for example the cytokines interleukin 1alpha and 1beta, and the basic and acidic fibroblast growth factors (7). One possibility for the export of such components is via ABC-transporter systems. These proteins comprise ATP-dependent and membrane bound proteins which contain membrane spanning helices. They are involved in protein specific binding and transport across membranes and are best characterised in bacterial systems. However, to date there is no direct evidence for a role of any mammalian ABC-transporters in proteins secretion.

Further, while certain proteins are secreted by a nonclassical pathway, the pattern of VP22 secretion is extremely unusual. While not wishing to be bound by any particular theory, the simplest interpretation of our results is that VP22 is secreted, but then taken up and concentrates in the nucleus of target cells. Again, there are no obvious nuclear localisation signals in VP22 although the protein has a predicted molecular weight of 32 k and may enter the nucleus without a requirement for a specific signal. Further studies on the determinants required within VP22 and of the physiological requirements within the cell should help clarify the pathway involved, and understanding how VP22 is secreted may contribute to an understanding of how other proteins are transported in non-classical export pathways.

These results open up the possibility of using the determinants involved in VP22 transport to enable the transport and efficient expression or uptake within a target cell population of other proteins or other molecules associated with the VP22 determinants. We have already shown that a short peptide (12 residues) can be linked to VP22 and the fusion protein still be transported to every cell in the monolayer. This result demonstrates that it is indeed feasible to promote the delivery of peptides by linking them to VP22.

Further, we have shown that a large protein (32 Kd), linked to VP22 can be imported into cells from the cell medium and is seen to accumulate in the nuclei.

Widespread utility of such ability can easily be envisaged.

For example it may be possible to link DNA binding proteins to the VP22 determinant(s), such that when delivered to a target cell population they will be efficiently expressed in a much larger population.

Other Utilities Include
Costimulatory Molecules and Cytokines are Required to Boost Vaccine Response by Host Recent data from the field of vaccine development highlights the requirement for costimulatory molecules and cytokines for vaccines to work effectively to boost the host immune response at the cellular level. Tumour cells do not express costimulatory molecules on their cell surface and this is the reason why there is no clonal expansion of CTL (cytotoxic T-lymphocytes) in the host, resulting in the patient's inability to effect tumour shrinkage without medical intervention.

Direct Stimulation of Cytotoxic T-Cell Response in Host

Delivery of foreign protein with anti-cancer properties to the nucleus. The foreign protein may be a tumour-specific antigen known to induce an immune (T-cell) response to the tumour.

The foreign protein may be delivered directly to the nucleus with VP22 molecules (this would also emulate a virus infection). The foreign protein would then be broken down to peptides in the proteosome of the cell. If the classical T-cell induction pathway is followed, the peptides are targeted through the ER and Golgi apparatus of the cell and presented on the cell surface in conjunction with MHC class-I molecules. Boosting the CTL response in patients has obvious applications to non-cancer therapy, particularly where diseases are caused by viral infection. The belief that inducing a strong CTL response in the host may lead to viral clearance from the body has recently gained scientific credibility.

Boost Immune Response with Delivery of MHC Molecule with Protein/Antigen to be Targeted It would be possible to solve the problem of MHC restriction in the population and boost cellular responses by targeting antigen plus HLA molecule. This application would also have non-cancer applications.

Modulation of Signal Transduction Pathways

Many signal transduction pathways operate by transferring an environmental signal, hormones, binding of ligands to membranes, stress (DNA damage, heat osmotic etc) to the nucleus to effect alterations in gene expression. It may be possible to use VP22 to mediate such signals by coupling the protein or peptide to signalling molecules. Delivery of the fusion protein, or the corresponding gene, will enhance signal because the fusion is also exported to neighbodring cells. For example, fusing VP22 to a dominant mutant of a plasma membrane associated signal effector (eg small GTPases and their effectors or apoptotic regulatory molecules) may effect the desired pathway not only in the recipient cell with the gene, but also in surrounding cells despite the absence of the gene in them. Many scenarios can be envisaged that are variations on the theme of modulation of signal transduction pathways.

The ability of VP22 to bind DNA in vitro and the ability for it to bind condensing chromosomes during mitosis provides for an application with regard to gene/DNA therapy. This application can take several forms:

a) virus infection where the gene for VP22 or variants thereof is inserted into the genomes of adenoviruses or retroviruses for delivery by infection. Likewise, a gene of a desired protein could also be inserted such that a fusion protein is expressed comprising VP22 and the protein of interest. VP22 would then serve to deliver the protein of interest to the surrounding population of cells. In this way the amount and therefore risk of such virus infection is reduced.

b) microinjection of nucleic acid coding for VP22 (or a variant thereof) and the protein of interest directly into a cell such that, once expressed, VP22 can transport the protein of interest into the surrounding population of cells.

c) liposome mediated infection where the gene for VP22 or various modifications including fusion proteins are incorporated into liposome vesicles for in vivo delivery.

Other techniques for introducing DNA into cells will be apparent to the skilled man, for example, direct scarification where the DNA is taken up directly by the tissue; receptor mediated DNA transfer; calcium phosphate mediated transfection; and ballistic delivery.

Efficient delivery of functional molecules is a desired aim in gene/protein therapy. This mechanism will have the additional advantage that the gene expressing VP22 will only be present in a small population of cells while the protein is present in a much wider population. This will be a useful factor where potentially harmful effects of the delivered gene are a consideration. Lower delivery of genes while maintaining high delivery of functional protein may be desirable. Virtually any application requiring or desiring efficient expression of test proteins can be envisaged in finding application for a VP22 delivery mechanism. Delivery of tumour suppressor proteins, enzymes and so on. We have also shown that it is possible to bind nucleic acids to VP22, and therefore in addition to DNA it may be possible to deliver antisense RNA ribozymes etc.

REFERENCES

1. Blaho, J. A., C. Mitchell, and B. Roizman. 1994. An amino acid sequence shared by the herpes simplex virus 1 alpha regulatory proteins 0,4,22 and 27 predicts the nucleotidylylation of the UL21, UL31, UL47, and UL49 gene products. J Biol Chem 269: 17401–10.
2. Blair, E. D., and R. W. Honess. 1983. DNA-binding proteins specified by herpes virus saimiri. J. Gen. Virol. 64: 2697–2715.
3. Chen, C., and H. Okayama. 1987. High-efficiency transformation of mammalian cells by plasmid DNA. Mol Cell Biol 7:2745–2752.
4. Elliott, G. D., and D. M. Meredith. 1992. The herpes simplex virus type 1 tegument protein VP22 is encoded by gene UL49. J Gen Virol 73:723–6.
5. Greaves, R. F., and P. O'Hare. 1990. Structural requirements in the herpes simplex virus type 1 transactivator Vmw65 for interaction with the cellular octamer-binding protein and target TAATGARAT sequences. J Virol 64:2716–2724.
6. Haarr, L., and S. Skulstad. 1994. The herpes simplex virus type 1 particle: structure and molecular functions. Review article. Apmis 102:321–46.
7. Klucher, K. 1993. Unusual routes of protein secretion: the easy way out. Trends in Cell Biol 3:421–426.
8. Knopf, K. W., and H. C. Kaerner. 1980. Virus specific basic phosphoproteins associated with herpes simplex virus type 1 (HSV-1) particles and the chromatin of HSV-1 infected cells. J. Gen. Virol. 46: 405–414.
9. Meredith, D. M., J. A. Lindsay, I. W. Halliburton, and G. R. Whittaker. 1991. Post-translational modification of the tegument proteins (VP13 and VP14) of herpes simplex virus type 1 by glycosylation and phosphorylation. J Gen Virol 72:2771–5.
10. Pinard, M. F., R. Simard, and V. Bibor-Hardy. 1987. DNA-binding proteins of herpes simplex virus type 1-infected BHK cell nuclear matrices. J Gen Virol 68:727–35.
11. Preston, C. M., and E. L. Notarianni. 1983. Poly(ADP-ribosyl)ation of a herpes simplex virus immediate early polypeptide. Virol. 131:492–501.
12. Rothman, J. E. 1994. Mechanisms of intracellular protein transport. Nature 372:55–63.

What is claimed is:

1. A composition of formula A-B wherein A and B are covalently associated, wherein A comprises a transport-active material selected from the group consisting of a herpesviral VP22 protein and a transport-active portion of a herpesviral VP22 protein, and B comprises a molecule that is desired to be delivered into a cell.

2. A composition according to claim 1 wherein A comprises the amino acid sequence set forth in SEQ ID NO:1.

3. A composition according to claim 1 wherein A comprises the amino acid sequence set forth in SEQ ID NO:2.

4. A composition according to claim 1 wherein B is a peptide.

5. A composition according to claim 1 wherein B is a nucleic acid molecule.

6. A method of delivering a desired molecule to a population of cells, the method comprising introducing into one or more cells in the population a composition comprising the desired molecule in association with a transport-active material selected from the group consisting of a herpesviral VP22 protein and a transport-active portion of a herpesviral VP22 protein.

7. The method of claim 6 where the desired molecule is covalently associated with the transport-active material.

8. The method of claim 6 where the desired molecule is covalently associated with an amino acid sequence selected from the group consisting of the amino acid sequence set forth in SEQ ID NO:1, and the amino acid sequence set forth in SEQ ID NO:2.

* * * * *

UNITED STATES PATENT AND TRADEMARK OFFICE
CERTIFICATE OF CORRECTION

PATENT NO.   : 6,184,038 B1
DATED        : February 6, 2001
INVENTOR(S)  : Peter Francis Joseph O'Hare and Gillian Daphne Elliott It is certified that error appears in the above-identified patent and that said Letters Patent is hereby corrected as shown below:

Column 13,
Line 42, "neighbodring" should read -- neighboring --.

Signed and Sealed this

Thirtieth Day of October, 2001

Attest:

NICHOLAS P. GODICI
Attesting Officer
Acting Director of the United States Patent and Trademark Office